US007091021B2

(12) United States Patent
Morin

(10) Patent No.: US 7,091,021 B2
(45) Date of Patent: Aug. 15, 2006

(54) INACTIVE VARIANTS OF THE HUMAN TELOMERASE CATALYTIC SUBUNIT

(75) Inventor: Gregg B. Morin, Davis, CA (US)

(73) Assignee: Geron Corporation, Menlo Park, CA (US)

( * ) Notice: Subject to any disclaimer, the term of this patent is extended or adjusted under 35 U.S.C. 154(b) by 462 days.

(21) Appl. No.: 09/990,080

(22) Filed: Nov. 21, 2001

(65) Prior Publication Data

US 2002/0102686 A1    Aug. 1, 2002

Related U.S. Application Data

(63) Continuation of application No. 09/128,354, filed on Aug. 3, 1998, now Pat. No. 6,337,200, which is a continuation-in-part of application No. 09/052,864, filed on Mar. 31, 1998, now abandoned.

(51) Int. Cl.
*C12N 9/12* (2006.01)
*C07K 1/00* (2006.01)
*A61K 38/00* (2006.01)
*A61K 38/51* (2006.01)
*C07H 21/04* (2006.01)

(52) U.S. Cl. .................. 435/194; 530/350; 514/12; 424/94.5; 536/23.5

(58) Field of Classification Search ................ 435/194; 530/350, 300, 324, 327, 388.21
See application file for complete search history.

(56) References Cited

U.S. PATENT DOCUMENTS

| 6,261,556 B1 | 7/2001 | Weinrich et al. ........... 424/94.5 |
| 6,261,836 B1 | 7/2001 | Cech et al. ................. 435/325 |
| 6,846,662 B1* | 1/2005 | Kilian et al. ................ 435/194 |
| 6,916,642 B1* | 7/2005 | Kilian et al. ................ 435/194 |

FOREIGN PATENT DOCUMENTS

| WO | WO 98/07838 | 2/1998 |
| WO | WO 98/21343 | 5/1998 |
| WO | WO 98/37181 | 8/1998 |
| WO | WO 99/01560 | 1/1999 |

OTHER PUBLICATIONS

Molecular Biology and Biotechnology. A Comprehensive Desk Reference, Meyers R. ed. Wiley-VCH, New York 1995, p. 187.*
Leem et al., The human telomerase gene: complete genomic sequence and analysis of tandem repeat polymorphisms in intronic regions, Oncogene, 2002, 21, 769-777.*
Li H. et al. Protein Phosphatase 2A Inhibits Nuclear Telomerase Activity in Human Brest Cancer Cells, J. Biol. Chem, 1997, 272, 16729-16732.*
Bachand et al., Functional Regions of Human Telomerse Reverse Transcriptase and Human Telomerase RNA Required for Telomerase Activity and RNA-Protein Interactions, Mol. and Cellular Biol. 21:1888 (2001).
Bodnar et al., Extension of Life-span by Induction of Telomerase into Normal Human Cells, Science 279:349 (1998).
Bryan et al., A Mutant of *Tetrahymena* Telomerase Reverse Transcriptase with Increased Processivity, J. Biol. Chem. 275:24199 (2000).
Bryan et al., Telomerase RNA Bound by Protein Notifs Specific to Telomerase Reverse Transcriptase, Molecular Cell 6:493 (2000).
Bryan et al., Telomerase reverse transcriptase genes identified in *Tetrahymena thermophila* and *Oxytricha trifallax*, Pro. Natl. Acad. Sci. USA 95:8479 (1998).
Colgin et al., The hTERTapha splice variant is a dominant negative inhibitor of telomerase activity, Neoplasia 2:426 (2000).
Farmery et al., Major Histocompatability Class I Folding, Assembly, and Degradation: A Paradigm for Two-Stage Quality Control in the Endoplasmic Reticulum, Progress in Nucleic Acid Res. 67:235 (2001).
Freidman et al., Essential functions of amino-terminal domains in the yeast telomerase catalytic subunit revealed by selection for variable mutants, Genes & Dev. 13:2863 (1999).
Haering et al., Analysis of telomerase catalytic subunit mutants *in vivo* and *In vitro* in *Schizosaccharomyces pombe*, PNAS 97:6367 (2000).
Hahn et al., Inhibition of telomerase limits the growth of human cancer cells, Nature Medicine 5:1164 (1999).
Harrington et al., Human telomerase contians evolutionarily consderved catalytic and structural subunits, Genes Dev. 11:3109 (1997).
Killan et al., Isolation of a Candidate Human Telomerase Catalytic Subunit Gene, Which Reveals Complex Splicing Patterns in Different Cell Types, Hum. Mol. Genet. 6:2011 (1997).
Lai et al., RNA Binding Domain of Telomerase Reverse Transcriptase, Mol. and Cellular Biol. 21:990 (2001).
Lingner et al., Reverse Transcriptase Motifs in the Catalytic Subunit of Telomerase, Science 276:561 (1997).
Morin, The Implications of Telomerase Biochemistry for Human Disease, Eur. J. Biol. Chem. 33:750(1998).
Myerson et al., hEST2, the Putative Human Telomerase Catalytic Subunit Gene Is Up-Regulated in Tumor Cells and during Immortalization, Cell 90:785 (1997).
Nakamura et al., Telomerase Catalytic Subunit Homologs from Fission Yeast and Human, Science 277:955 (1997).
Perez et al., Human formyl peptide receptor ligand binding domain(s). Studies using an improved mutagenesis/expression vector reveal a novel mechanism for the regulation of receptor occupancy, J. Biol. Chem. 269:22485 (1994).

(Continued)

*Primary Examiner*—Rebecca E. Prouty
*Assistant Examiner*—Malgorzata A. Walicka
(74) *Attorney, Agent, or Firm*—J. Michael Schiff; David J. Earp

(57) ABSTRACT

The invention provides compositions and methods related to human telomerase reverse transcriptase (hTRT), the catalytic protein subunit of human telomerase. Catalytically active and inactive human telomerase reverse transcriptase variants comprising deletions or other mutations are provided.

11 Claims, 2 Drawing Sheets

OTHER PUBLICATIONS

Solheim et al., Class I MHC molecules: assembly and antigen presentation, Immun. Reviews 172:11 (1999).

Weinrich et al., Reconstitution of Human Telomerase with the Template RNA Component hTR and the Catalytic Protein Subunit hTRT, Nat. Genet. 17:498 (1997).

Xia et al., Identificationof Funtionally Important Domains in the N-Terminal Region of Telomerase Reverse Transcriptase, Mod. and Cellular Biol. 20:5196 (2000).

Zakharova et al., Structural Constraints in the HIV-1 Reverse Transcriptase-Primer/Template Complex for the Initiation of DNA Synthesis from Primer $tRNA^{Lys3}$, Biochem. 37:13343 (1998).

* cited by examiner

```
MPRAPRCRAVRSLLRSHYREVLPLATFVRRLGPQGWRLVQRGDP
AAFRALVAQCLVCVPWDARPPPAAPSFRQVSCLKELVARVLQRL
CERGAKNVLAFGFALLDGARGGPPEAFTTSVRSYLPNTVTDALR
GSGAWGLLLRRVGDDVLVHLLARCALFVLVAPSCAYQVCGPPLY
QLGAATQARPPPHASGPRRRLGCERAWNHSVREAGVPLGLPAPG
ARRRGGSASRSLPLPKRPRRGAAPEPERTPVGQGSWAHPGRTRG
PSDRGFCVVSPARPAEEATSLEGALSGTRHSHPSVGRQHHAGPP
STSRPPRPWDTPCPPVYAETKHFLYSSGDKEQLRPSFLLSSLRP
SLTGARRLVETIFLGSRPWMPGTPRRLPRLPQRYWQMRPLFLEL
LGNHAQCPYGVLLKTHCPLRAAVTPAAGVCAREKPQGSVAAPEE
EDTDPRRLVQLLRQHSSPWQVYGFVRACLRRLVPPGLWGSRHNE
RRFLRNTKKFISLGKHAKLSLQELTWKMSVRDCAWLRRSPGVGC
VPAAEHRLREEILAKFLHWLMSVYVVELLRSFFYVTETTFQKNR
LFFYRKSVWSKLQSIGIRQHLKRVQLRELSEAEVRQHREARPAL
LTSRLRFIPKPDGLRPIVNMDYVVGARTFRREKRAERLTSRVKA
LFSVLNYERARRPGLLGASVLGLDDIHRAWRTFVLRVRAQDPPP
ELYFVKVDVTGAYDTIPQDRLTEVIASIIKPQNTYCVRRYAVVQ
KAAHGHVRKAFKSHVSTLTDLQPYMRQFVAHLQETSPLRDAVVI
EQSSSLNEASSGLFDVFLRFMCHHAVRIRGKSYVQCQGIPQGSI
LSTLLCSLCYGDMENKLFAGIRRDGLLLRLVDDFLLVTPHLTHA
KTFLRTLVRGVPEYGCVVNLRKTVVNFPVEDEALGGTAFVQMPA
HGLFPWCGLLLDTRTLEVQSDYSSYARTSIRASLTFNRGFKAGR
NMRRKLFGVLRLKCHSLFLDLQVNSLQTVCTNIYKILLLQAYRF
HACVLQLPFHQQVWKNPTFFLRVISDTASLCYSILKAKNAGMSL
GAKGAAGPLPSEAVQWLCHQAFLLKLTRHRVTYVPLLGSLRTAQ
TQLSRKLPGTTLTALEAAANPALPSDFKTILD
```

FIG. 1

```
   1 gcagcgctgc gtcctgctgc gcacgtggga agccctggcc ccggccaccc ccgcgatgcc
  61 gcgcgctccc cgctgccgag ccgtgcgctc cctgctgcgc agccactacc gcgaggtgct
 121 gccgctggcc acgttcgttgc ggcgctgggg gccccaggggc tggcggctgg tgcagcgcgg
 181 ggacccggcg gctttccgcg cgctggtcgg ccagtgcctg gtgtgcgtgc cctgggacgc
 241 acggccgccc cccgccgccc cctccttccg ccaggtgtcc tgcctgaagg agctggtggc
 301 ccgagtgctg cagaggctgt gcgagcgcgg cgcgaagaac gtgctggcct tcggcttcgc
 361 gctgctggac ggggcccgcg ggggcccccc cgaggccttc accaccagcg tgcgcagcta
 421 cctgcccaac acggtgaccg acgcactgcg ggggagcggg gcgtggggggc tgctgctgcg
 481 ccgcgtgggc gacgacgtgc tggttcacct gctggcacgc tgcgcgctct ttgtgctggt
 541 ggctcccagc tgcgcctacc aggtgtgcgg gccgccgctg taccagctcg gcgctgccac
 601 tcaggcccgg cccccgccac acgctagtgg accccgaagg cgtctgggat gcgaacgggc
 661 ctggaaccat agcgtcaggg aggccgggggt cccccctgggc ctgccagccc cgggtgcgag
 721 gaggcgcggg ggcagtgcca gccgaagtct gccgttgccc aagaggccca ggcgtggcgc
 781 tgcccctgag ccggagcgga cgcccgttgg gcagggggtcc tgggcccacc cgggcaggac
 841 gcgtggaccg agtgaccgtg gtttctgtgt ggtgtcacct gccagacccg ccgaagaagc
 901 cacctctttg gagggtgcgc tctctggcac gcgccactcc cacccatccg tgggccgcca
 961 gcaccacgcg ggcccccat ccacatcgcg gccaccacgt ccctgggaca cgccttgtcc
1021 cccggtgtac gccgagacca agcacttcct ctactcctca ggcgacaagg agcagctgcg
1081 gccctccttc ctactcagct ctctgaggcc cagcctgact ggcgctcgga ggctcgtgga
1141 gaccatcttt ctgggttcca ggcctggat gccagggact ccccgcaggt tgcccgccct
1201 gccccagcgc tactggcaaa tgcgcccct gtttctggag ctgcttggga accacgcga
1261 gtgccctac ggggtgctcc tcaagacgca ctgcccgctg cgagctgcgg tcaccccagc
1321 agccggtgtc tgtgcccggg agaagcccca gggctctgtg gcggccccg aggaggagga
1381 cacagacccc cgtcgcctgg tgcagctgct ccgccagcac agcagcccct ggcaggtgta
1441 cggcttcgtg cgggcctgcc tgcgccggct ggtgcccca ggcctctggg gctccaggca
1501 caacgaacgc cgcttcctca ggaacaccaa gaagttcatc tccctgggga agcatgccaa
1561 gctctcgctc caggagctga cgtggaagat gagcgtgcgg gactgcgctt ggctgcgcag
1621 gagcccaggg gttggctgtg ttccggccgc agagcaccgt ctgcgtgagg agatcctggc
1681 caagttcctg cactgcgtga tgagtgtcgta cgtcgtcagg ctgctcaggt ctttctttta
1741 tgtcacggag accacgtttc aaaagaacag gctcttttc taccgaaga gtgtctggag
1801 caagttgcaa agcattggaa tcagacagca cttgaagagg gtgcagctgc gggagctgtc
1861 ggaagcagag gtcaggcagc atcgggaagc caggcccgcc ctgctgacgt ccagactccg
1921 cttcatcccc aagcctgacg ggctgcggcc gattgtgaac atggactacg tcgtgggagc
1981 cagaacgttc cgcagagaaa agagggccga gcgtctcacc tcgagggtga aggcactgtt
2041 cagcgtgctc aactacgagc gggcgcggcg ccccggcctc ctgggcgcct ctgtgctggg
2101 cctggacgat atccacaggg cctggccac cttcgtgctg cgtgtgcggg ccaggaccc
2161 gccgcctgag ctgtactttg tcaaggtgga tgtgacgggc gcgtacgaca ccatccccca
2221 ggacaggctc acggaggtca tcgccagcat catcaaaccc cagaacacgt actgcgtgcg
2281 tcggtatgcc gtggtccaga aggccgccca tgggcacgtc cgcaaggcct tcaagagcca
2341 cgtctctacc ttgacagacc tccagccgta catgcgacag ttcgtggctc acctgcagga
2401 gaccagcccg ctgagggatg ccgtcgtcat cgagcagagc tcctccctga atgaggccag
2461 cagtggcctc ttcgacgtct tcctacgctt catgtgccac cacgccgtgc gcatcagggg
2521 caagtcctac gtccagtgcc agggggatccc gcagggctcc atcctctcca cgctgctctg
2581 cagcctgtgc tacgcgcaca tggagaacaa gctgtttgcg gggattgggg gggacgggct
2641 gctcctgcgt ttggtggatg attttcttgtt ggtgacacct caccccaccc acgcgaaaac
2701 cttcctcagg accctggtcc gaggtgtccc tgagtatggc tgcgtggtga acttgcggaa
2761 gacagtggtg aacttccctg tagaagacga ggccctgggt ggcacggctt ttgttcagat
2821 gccggccac ggcctattcc cctggtgcgg cctgctgctg ataccggga ccctggaggt
2881 gcagagcgac tactccagct atgcccggac ctccatcaga gccagtctca ccttcaaccg
2941 cggcttcaag gctggggagga acatgcgtcg caaactcttt ggggtcttgc ggctgaagtg
3001 tcacagcctg tttctggatt tgcaggtgaa cagcctccag acggtgtgca ccaacatcta
3061 caagatcctc ctgctgcagg cgtacaggtt tcacgcatgt gtgctgcagc tcccattttca
3121 tcagcaagtt tggaagaacc ccacatttt cctgcgcgtc atctctgaca cggcctccct
3181 ctgctactcc atcctgaaag ccaagaacgc agggatgtcg ctgggggcca agggcgccgc
3241 cggccctctg ccctccgagg ccgtgcagtg gctgtgccac caagcattcc tgctcaagct
3301 gactcgacac cgtgtcacct acgtgccact cctggggtca ctcaggacag cccagacgca
3361 gctgagtcgg aagctcccgg ggacgacgct gactgccctg gaggccgcag ccaacccggc
3421 actgccctca gacttcaaga ccatcctgga ctgatggcca cccgccaca gccaggccga
3481 gagcagacac cagcagccct gtcacgccgg gctctacgtc caggggagggg aggggcggcc
3541 cacacccagg cccgcaccgc tgggagtcgt aggcctgagt gagtgtttgg ccgaggcctg
3601 catgtccggc tgaaggctga gtgtccgct gaggcctgag cgagtgtcca gccaagggct
3661 gagtgtccag cacacctgcc gtcttcactt ccccacaggc tggcgctcgg ctccacccca
3721 gggccagctt ttcctcacca ggagcccggc ttccactccc cacataggaa tagtccatcc
3781 ccagattcgc cattgttcac ccctcgccct gccctccttt gccttccacc ccaccatcc
3841 aggtggagac cctgagaagg accctgggag ctctgggaat tggagtgac caaaggtgtg
3901 ccctgtacac aggcgaggac cctgcacctg gatgggggtc cctgtgggtc aaattggggg
3961 gaggtgctgt gggagtaaaa tactgaatat atgagttttt cagttttgaa aaaaa
```

FIG. 2

SEQUENCE LISTING

```
<160> NUMBER OF SEQ ID NOS: 21

<210> SEQ ID NO 1
<211> LENGTH: 4015
<212> TYPE: DNA
<213> ORGANISM: Homo sapiens
<220> FEATURE:
<221> NAME/KEY: CDS
<222> LOCATION: (56)..(3454)
<223> OTHER INFORMATION: human telomerase reverse transcriptase (hTRT)
      cDNA

<400> SEQUENCE: 1
gcagcgctgc gtcctgctgc gcacgtggga agccctggcc ccggccaccc ccgcg atg        58
                                                              Met
                                                               1 ccg cgc gct ccc cgc tgc cga gcc gtg cgc tcc ctg ctg cgc agc cac         106
Pro Arg Ala Pro Arg Cys Arg Ala Val Arg Ser Leu Leu Arg Ser His
         5                  10                  15 tac cgc gag gtg ctg ccg ctg gcc acg ttc gtg cgg cgc ctg ggg ccc         154
Tyr Arg Glu Val Leu Pro Leu Ala Thr Phe Val Arg Arg Leu Gly Pro
     20                  25                  30 cag ggc tgg cgg ctg gtg cag cgc ggg gac ccg gcg gct ttc cgc gcg         202
Gln Gly Trp Arg Leu Val Gln Arg Gly Asp Pro Ala Ala Phe Arg Ala
 35                  40                  45 ctg gtg gcc cag tgc ctg gtg tgc gtg ccc tgg gac gca cgg ccg ccc         250
Leu Val Ala Gln Cys Leu Val Cys Val Pro Trp Asp Ala Arg Pro Pro
 50                  55                  60                  65 ccc gcc gcc ccc tcc ttc cgc cag gtg tcc tgc ctg aag gag ctg gtg         298
Pro Ala Ala Pro Ser Phe Arg Gln Val Ser Cys Leu Lys Glu Leu Val
                 70                  75                  80 gcc cga gtg ctg cag agg ctg tgc gag cgc ggc gcg aag aac gtg ctg         346
Ala Arg Val Leu Gln Arg Leu Cys Glu Arg Gly Ala Lys Asn Val Leu
             85                  90                  95 gcc ttc ggc ttc gcg ctg ctg gac ggg gcc cgc ggg ggc ccc ccc gag         394
Ala Phe Gly Phe Ala Leu Leu Asp Gly Ala Arg Gly Gly Pro Pro Glu
         100                 105                 110 gcc ttc acc acc agc gtg cgc agc tac ctg ccc aac acg gtg acc gac         442
Ala Phe Thr Thr Ser Val Arg Ser Tyr Leu Pro Asn Thr Val Thr Asp
     115                 120                 125 gca ctg cgg ggg agc ggg gcg tgg ggg ctg ctg ctg cgc cgc gtg ggc         490
Ala Leu Arg Gly Ser Gly Ala Trp Gly Leu Leu Leu Arg Arg Val Gly
 130                 135                 140                 145 gac gac gtg ctg gtt cac ctg ctg gca cgc tgc gcg ctc ttt gtg ctg         538
Asp Asp Val Leu Val His Leu Leu Ala Arg Cys Ala Leu Phe Val Leu
                 150                 155                 160 gtg gct ccc agc tgc gcc tac cag gtg tgc ggg ccg ccg ctg tac cag         586
Val Ala Pro Ser Cys Ala Tyr Gln Val Cys Gly Pro Pro Leu Tyr Gln
             165                 170                 175 ctc ggc gct gcc act cag gcc cgg ccc ccg cca cac gct agt gga ccc         634
Leu Gly Ala Ala Thr Gln Ala Arg Pro Pro Pro His Ala Ser Gly Pro
         180                 185                 190
```

-continued

| | |
|---|---|
| cga agg cgt ctg gga tgc gaa cgg gcc tgg aac cat agc gtc agg gag<br>Arg Arg Arg Leu Gly Cys Glu Arg Ala Trp Asn His Ser Val Arg Glu<br>195                          200                        205 | 682 |
| gcc ggg gtc ccc ctg ggc ctg cca gcc ccg ggt gcg agg agg cgc ggg<br>Ala Gly Val Pro Leu Gly Leu Pro Ala Pro Gly Ala Arg Arg Arg Gly<br>210                          215                        220                        225 | 730 |
| ggc agt gcc agc cga agt ctg ccg ttg ccc aag agg ccc agg cgt ggc<br>Gly Ser Ala Ser Arg Ser Leu Pro Leu Pro Lys Arg Pro Arg Arg Gly<br>                    230                        235                        240 | 778 |
| gct gcc cct gag ccg gag cgg acg ccc gtt ggg cag ggg tcc tgg gcc<br>Ala Ala Pro Glu Pro Glu Arg Thr Pro Val Gly Gln Gly Ser Trp Ala<br>                        245                        250                        255 | 826 |
| cac ccg ggc agg acg cgt gga ccg agt gac cgt ggt ttc tgt gtg gtg<br>His Pro Gly Arg Thr Arg Gly Pro Ser Asp Arg Gly Phe Cys Val Val<br>                  260                        265                        270 | 874 |
| tca cct gcc aga ccc gcc gaa gaa gcc acc tct ttg gag ggt gcg ctc<br>Ser Pro Ala Arg Pro Ala Glu Glu Ala Thr Ser Leu Glu Gly Ala Leu<br>275                          280                        285 | 922 |
| tct ggc acg cgc cac tcc cac cca tcc gtg ggc cgc cag cac cac gcg<br>Ser Gly Thr Arg His Ser His Pro Ser Val Gly Arg Gln His His Ala<br>290                          295                        300                        305 | 970 |
| ggc ccc cca tcc aca tcg cgg cca cca cgt ccc tgg gac acg cct tgt<br>Gly Pro Pro Ser Thr Ser Arg Pro Pro Arg Pro Trp Asp Thr Pro Cys<br>                      310                        315                        320 | 1018 |
| ccc ccg gtg tac gcc gag acc aag cac ttc ctc tac tcc tca ggc gac<br>Pro Pro Val Tyr Ala Glu Thr Lys His Phe Leu Tyr Ser Ser Gly Asp<br>                  325                        330                        335 | 1066 |
| aag gag cag ctg cgg ccc tcc ttc cta ctc agc tct ctg agg ccc agc<br>Lys Glu Gln Leu Arg Pro Ser Phe Leu Leu Ser Ser Leu Arg Pro Ser<br>                      340                        345                        350 | 1114 |
| ctg act ggc gct cgg agg ctc gtg gag acc atc ttt ctg ggt tcc agg<br>Leu Thr Gly Ala Arg Arg Leu Val Glu Thr Ile Phe Leu Gly Ser Arg<br>355                          360                        365 | 1162 |
| ccc tgg atg cca ggg act ccc cgc agg ttg ccc cgc ctg ccc cag cgc<br>Pro Trp Met Pro Gly Thr Pro Arg Arg Leu Pro Arg Leu Pro Gln Arg<br>370                          375                        380                        385 | 1210 |
| tac tgg caa atg cgg ccc ctg ttt ctg gag ctg ctt ggg aac cac gcg<br>Tyr Trp Gln Met Arg Pro Leu Phe Leu Glu Leu Leu Gly Asn His Ala<br>                      390                        395                        400 | 1258 |
| cag tgc ccc tac ggg gtg ctc ctc aag acg cac tgc ccg ctg cga gct<br>Gln Cys Pro Tyr Gly Val Leu Leu Lys Thr His Cys Pro Leu Arg Ala<br>                  405                        410                        415 | 1306 |
| gcg gtc acc cca gca gcc ggt gtc tgt gcc cgg gag aag ccc cag ggc<br>Ala Val Thr Pro Ala Ala Gly Val Cys Ala Arg Glu Lys Pro Gln Gly<br>                      420                        425                        430 | 1354 |
| tct gtg gcg gcc ccc gag gag gag gac aca gac ccc cgt cgc ctg gtg<br>Ser Val Ala Ala Pro Glu Glu Glu Asp Thr Asp Pro Arg Arg Leu Val<br>435                          440                        445 | 1402 |
| cag ctg ctc cgc cag cac agc agc ccc tgg cag gtg tac ggc ttc gtg<br>Gln Leu Leu Arg Gln His Ser Ser Pro Trp Gln Val Tyr Gly Phe Val<br>450                          455                        460                        465 | 1450 |
| cgg gcc tgc ctg cgc cgg ctg gtg ccc cca ggc ctg tgg ggc tcc agg<br>Arg Ala Cys Leu Arg Arg Leu Val Pro Pro Gly Leu Trp Gly Ser Arg<br>                      470                        475                        480 | 1498 |
| cac aac gaa cgc cgc ttc ctc agg aac acc aag aag ttc atc tcc ctg<br>His Asn Glu Arg Arg Phe Leu Arg Asn Thr Lys Lys Phe Ile Ser Leu<br>                  485                        490                        495 | 1546 |
| ggg aag cat gcc aag ctc tcg ctg cag gag ctg acg tgg aag atg agc<br>Gly Lys His Ala Lys Leu Ser Leu Gln Glu Leu Thr Trp Lys Met Ser<br>                      500                        505                        510 | 1594 |

|  |  |
|---|---|
| gtg cgg gac tgc gct tgg ctg cgc agg agc cca ggg gtt ggc tgt gtt<br>Val Arg Asp Cys Ala Trp Leu Arg Arg Ser Pro Gly Val Gly Cys Val<br>515                    520                   525 | 1642 |
| ccg gcc gca gag cac cgt ctg cgt gag gag atc ctg gcc aag ttc ctg<br>Pro Ala Ala Glu His Arg Leu Arg Glu Glu Ile Leu Ala Lys Phe Leu<br>530                    535                   540                   545 | 1690 |
| cac tgg ctg atg agt gtg tac gtc gtc gag ctg ctc agg tct ttc ttt<br>His Trp Leu Met Ser Val Tyr Val Val Glu Leu Leu Arg Ser Phe Phe<br>                   550                   555                   560 | 1738 |
| tat gtc acg gag acc acg ttt caa aag aac agg ctc ttt ttc tac cgg<br>Tyr Val Thr Glu Thr Thr Phe Gln Lys Asn Arg Leu Phe Phe Tyr Arg<br>            565                   570                   575 | 1786 |
| aag agt gtc tgg agc aag ttg caa agc att gga atc aga cag cac ttg<br>Lys Ser Val Trp Ser Lys Leu Gln Ser Ile Gly Ile Arg Gln His Leu<br>580                    585                   590 | 1834 |
| aag agg gtg cag ctg cgg gag ctg tcg gaa gca gag gtc agg cag cat<br>Lys Arg Val Gln Leu Arg Glu Leu Ser Glu Ala Glu Val Arg Gln His<br>595                    600                   605 | 1882 |
| cgg gaa gcc agg ccc gcc ctg ctg acg tcc aga ctc cgc ttc atc ccc<br>Arg Glu Ala Arg Pro Ala Leu Leu Thr Ser Arg Leu Arg Phe Ile Pro<br>610                    615                   620                   625 | 1930 |
| aag cct gac ggg ctg cgg ccg att gtg aac atg gac tac gtc gtg gga<br>Lys Pro Asp Gly Leu Arg Pro Ile Val Asn Met Asp Tyr Val Val Gly<br>                   630                   635                   640 | 1978 |
| gcc aga acg ttc cgc aga gaa aag agg gcc gag cgt ctc acc tcg agg<br>Ala Arg Thr Phe Arg Arg Glu Lys Arg Ala Glu Arg Leu Thr Ser Arg<br>            645                   650                   655 | 2026 |
| gtg aag gca ctg ttc agc gtg ctc aac tac gag cgg gcg cgg cgc ccc<br>Val Lys Ala Leu Phe Ser Val Leu Asn Tyr Glu Arg Ala Arg Arg Pro<br>660                    665                   670 | 2074 |
| ggc ctc ctg ggc gcc tct gtg ctg ggc ctg gac gat atc cac agg gcc<br>Gly Leu Leu Gly Ala Ser Val Leu Gly Leu Asp Asp Ile His Arg Ala<br>675                    680                   685 | 2122 |
| tgg cgc acc ttc gtg ctg cgt gtg cgg gcc cag gac ccg ccg cct gag<br>Trp Arg Thr Phe Val Leu Arg Val Arg Ala Gln Asp Pro Pro Pro Glu<br>690                    695                   700                   705 | 2170 |
| ctg tac ttt gtc aag gtg gat gtg acg ggc gcg tac gac acc atc ccc<br>Leu Tyr Phe Val Lys Val Asp Val Thr Gly Ala Tyr Asp Thr Ile Pro<br>                   710                   715                   720 | 2218 |
| cag gac agg ctc acg gag gtc atc gcc agc atc atc aaa ccc cag aac<br>Gln Asp Arg Leu Thr Glu Val Ile Ala Ser Ile Ile Lys Pro Gln Asn<br>            725                   730                   735 | 2266 |
| acg tac tgc gtg cgt cgg tat gcc gtg gtc cag aag gcc gcc cat ggg<br>Thr Tyr Cys Val Arg Arg Tyr Ala Val Val Gln Lys Ala Ala His Gly<br>740                    745                   750 | 2314 |
| cac gtc cgc aag gcc ttc aag agc cac gtc tct acc ttg aca gac ctc<br>His Val Arg Lys Ala Phe Lys Ser His Val Ser Thr Leu Thr Asp Leu<br>755                    760                   765 | 2362 |
| cag ccg tac atg cga cag ttc gtg gct cac ctg cag gag acc agc ccg<br>Gln Pro Tyr Met Arg Gln Phe Val Ala His Leu Gln Glu Thr Ser Pro<br>770                    775                   780                   785 | 2410 |
| ctg agg gat gcc gtc gtc atc gag cag agc tcc tcc ctg aat gag gcc<br>Leu Arg Asp Ala Val Val Ile Glu Gln Ser Ser Ser Leu Asn Glu Ala<br>                   790                   795                   800 | 2458 |
| agc agt ggc ctc ttc gac gtc ttc cta cgc ttc atg tgc cac cac gcc<br>Ser Ser Gly Leu Phe Asp Val Phe Leu Arg Phe Met Cys His His Ala<br>            805                   810                   815 | 2506 |
| gtg cgc atc agg ggc aag tcc tac gtc cag tgc cag ggg atc ccg cag<br>Val Arg Ile Arg Gly Lys Ser Tyr Val Gln Cys Gln Gly Ile Pro Gln<br>820                    825                   830 | 2554 |

```
ggc tcc atc ctc tcc acg ctg ctc tgc agc ctg tgc tac ggc gac atg    2602
Gly Ser Ile Leu Ser Thr Leu Leu Cys Ser Leu Cys Tyr Gly Asp Met
    835                 840                 845 gag aac aag ctg ttt gcg ggg att cgg cgg gac ggg ctg ctc ctg cgt    2650
Glu Asn Lys Leu Phe Ala Gly Ile Arg Arg Asp Gly Leu Leu Leu Arg
850                 855                 860                 865 ttg gtg gat gat ttc ttg ttg gtg aca cct cac ctc acc cac gcg aaa    2698
Leu Val Asp Asp Phe Leu Leu Val Thr Pro His Leu Thr His Ala Lys
                870                 875                 880 acc ttc ctc agg acc ctg gtc cga ggt gtc cct gag tat ggc tgc gtg    2746
Thr Phe Leu Arg Thr Leu Val Arg Gly Val Pro Glu Tyr Gly Cys Val
            885                 890                 895 gtg aac ttg cgg aag aca gtg gtg aac ttc cct gta gaa gac gag gcc    2794
Val Asn Leu Arg Lys Thr Val Val Asn Phe Pro Val Glu Asp Glu Ala
        900                 905                 910 ctg ggt ggc acg gct ttt gtt cag atg ccg gcc cac ggc cta ttc ccc    2842
Leu Gly Gly Thr Ala Phe Val Gln Met Pro Ala His Gly Leu Phe Pro
    915                 920                 925 tgg tgc ggc ctg ctg ctg gat acc cgg acc ctg gag gtg cag agc gac    2890
Trp Cys Gly Leu Leu Leu Asp Thr Arg Thr Leu Glu Val Gln Ser Asp
930                 935                 940                 945 tac tcc agc tat gcc cgg acc tcc atc aga gcc agt ctc acc ttc aac    2938
Tyr Ser Ser Tyr Ala Arg Thr Ser Ile Arg Ala Ser Leu Thr Phe Asn
                950                 955                 960 cgc ggc ttc aag gct ggg agg aac atg cgt cgc aaa ctc ttt ggg gtc    2986
Arg Gly Phe Lys Ala Gly Arg Asn Met Arg Arg Lys Leu Phe Gly Val
            965                 970                 975 ttg cgg ctg aag tgt cac agc ctg ttt ctg gat ttg cag gtg aac agc    3034
Leu Arg Leu Lys Cys His Ser Leu Phe Leu Asp Leu Gln Val Asn Ser
        980                 985                 990 ctc cag acg gtg tgc acc aac atc tac aag atc ctc ctg ctg cag gcg    3082
Leu Gln Thr Val Cys Thr Asn Ile Tyr Lys Ile Leu Leu Leu Gln Ala
    995                 1000                1005 tac agg ttt cac gca tgt gtg ctg cag ctc cca ttt cat cag caa gtt    3130
Tyr Arg Phe His Ala Cys Val Leu Gln Leu Pro Phe His Gln Gln Val
1010                1015                1020                1025 tgg aag aac ccc aca ttt ttc ctg cgc gtc atc tct gac acg gcc tcc    3178
Trp Lys Asn Pro Thr Phe Phe Leu Arg Val Ile Ser Asp Thr Ala Ser
                1030                1035                1040 ctc tgc tac tcc atc ctg aaa gcc aag aac gca ggg atg tcg ctg ggg    3226
Leu Cys Tyr Ser Ile Leu Lys Ala Lys Asn Ala Gly Met Ser Leu Gly
            1045                1050                1055 gcc aag ggc gcc gcc ggc cct ctg ccc tcc gag gcc gtg cag tgg ctg    3274
Ala Lys Gly Ala Ala Gly Pro Leu Pro Ser Glu Ala Val Gln Trp Leu
        1060                1065                1070 tgc cac caa gca ttc ctg ctc aag ctg act cga cac cgt gtc acc tac    3322
Cys His Gln Ala Phe Leu Leu Lys Leu Thr Arg His Arg Val Thr Tyr
    1075                1080                1085 gtg cca ctc ctg ggg tca ctc agg aca gcc cag acg cag ctg agt cgg    3370
Val Pro Leu Leu Gly Ser Leu Arg Thr Ala Gln Thr Gln Leu Ser Arg
1090                1095                1100                1105 aag ctc ccg ggg acg acg ctg act gcc ctg gag gcc gca gcc aac ccg    3418
Lys Leu Pro Gly Thr Thr Leu Thr Ala Leu Glu Ala Ala Ala Asn Pro
                1110                1115                1120 gca ctg ccc tca gac ttc aag acc atc ctg gac tga tggccaccg          3464
Ala Leu Pro Ser Asp Phe Lys Thr Ile Leu Asp
            1125                1130 cccacagcca ggccgagagc agacaccagc agccctgtca cgccgggctc tacgtcccag  3524
ggagggaggg gcggcccaca cccaggcccg caccgctggg agtctgaggc ctgagtgagt  3584
```

```
gtttggccga ggcctgcatg tccggctgaa ggctgagtgt ccggctgagg cctgagcgag   3644
tgtccagcca agggctgagt gtccagcaca cctgccgtct tcacttcccc acaggctggc   3704
gctcggctcc accccagggc cagcttttcc tcaccaggag cccggcttcc actccccaca   3764
taggaatagt ccatcccccag attcgccatt gttcacccct cgccctgccc tcctttgcct   3824
tccaccccca ccatccaggt ggagaccctg agaaggaccc tgggagctct gggaatttgg   3884
agtgaccaaa ggtgtgccct gtacacaggc gaggaccctg cacctggatg ggggtccctg   3944
tgggtcaaat tggggggagg tgctgtggga gtaaaatact gaatatatga gttttttcagt  4004 tttgaaaaaa a                                                        4015

<210> SEQ ID NO 2
<211> LENGTH: 1132
<212> TYPE: PRT
<213> ORGANISM: Homo sapiens

<400> SEQUENCE: 2
```

| Met<br>1 | Pro | Arg | Ala | Pro<br>5 | Arg | Cys | Arg | Ala | Val<br>10 | Arg | Ser | Leu | Leu | Arg<br>15 | Ser |
|---|---|---|---|---|---|---|---|---|---|---|---|---|---|---|---|
| His | Tyr | Arg | Glu<br>20 | Val | Leu | Pro | Leu | Ala<br>25 | Thr | Phe | Val | Arg | Arg<br>30 | Leu | Gly |
| Pro | Gln | Gly<br>35 | Trp | Arg | Leu | Val | Gln<br>40 | Arg | Gly | Asp | Pro | Ala<br>45 | Ala | Phe | Arg |
| Ala | Leu<br>50 | Val | Ala | Gln | Cys | Leu<br>55 | Val | Cys | Val | Pro | Trp<br>60 | Asp | Ala | Arg | Pro |
| Pro<br>65 | Pro | Ala | Ala | Pro | Ser<br>70 | Phe | Arg | Gln | Val | Ser<br>75 | Cys | Leu | Lys | Glu | Leu<br>80 |
| Val | Ala | Arg | Val | Leu<br>85 | Gln | Arg | Leu | Cys | Glu<br>90 | Arg | Gly | Ala | Lys | Asn<br>95 | Val |
| Leu | Ala | Phe | Gly<br>100 | Phe | Ala | Leu | Leu | Asp<br>105 | Gly | Ala | Arg | Gly | Gly<br>110 | Pro | Pro |
| Glu | Ala | Phe<br>115 | Thr | Thr | Ser | Val | Arg<br>120 | Ser | Tyr | Leu | Pro | Asn<br>125 | Thr | Val | Thr |
| Asp | Ala<br>130 | Leu | Arg | Gly | Ser | Gly<br>135 | Ala | Trp | Gly | Leu | Leu<br>140 | Leu | Arg | Arg | Val |
| Gly<br>145 | Asp | Asp | Val | Leu | Val<br>150 | His | Leu | Leu | Ala | Arg<br>155 | Cys | Ala | Leu | Phe | Val<br>160 |
| Leu | Val | Ala | Pro | Ser<br>165 | Cys | Ala | Tyr | Gln | Val<br>170 | Cys | Gly | Pro | Pro | Leu<br>175 | Tyr |
| Gln | Leu | Gly | Ala<br>180 | Ala | Thr | Gln | Ala | Arg<br>185 | Pro | Pro | Pro | His | Ala<br>190 | Ser | Gly |
| Pro | Arg | Arg<br>195 | Arg | Leu | Gly | Cys | Glu<br>200 | Arg | Ala | Trp | Asn | His<br>205 | Ser | Val | Arg |
| Glu | Ala<br>210 | Gly | Val | Pro | Leu | Gly<br>215 | Leu | Pro | Ala | Pro | Gly<br>220 | Ala | Arg | Arg | Arg |
| Gly<br>225 | Gly | Ser | Ala | Ser | Arg<br>230 | Ser | Leu | Pro | Leu | Pro<br>235 | Lys | Arg | Pro | Arg | Arg<br>240 |
| Gly | Ala | Ala | Pro | Glu<br>245 | Pro | Glu | Arg | Thr | Pro<br>250 | Val | Gly | Gln | Gly | Ser<br>255 | Trp |
| Ala | His | Pro | Gly<br>260 | Arg | Thr | Arg | Gly | Pro<br>265 | Ser | Asp | Arg | Gly | Phe<br>270 | Cys | Val |
| Val | Ser | Pro<br>275 | Ala | Arg | Pro | Ala | Glu<br>280 | Glu | Ala | Thr | Ser | Leu<br>285 | Glu | Gly | Ala |

-continued

```
Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Ser Ser Leu Arg Pro
                340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
    435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
    515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro Pro
    690                 695                 700
```

-continued

```
Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
            725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
                835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
                915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
                980                 985                 990

Ser Leu Gln Thr Val Cys Thr Asn Ile Tyr Lys Ile Leu Leu Leu Gln
                995                 1000                1005

Ala Tyr Arg Phe His Ala Cys Val Leu Gln Leu Pro Phe His Gln Gln
    1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
                1045                1050                1055

Gly Ala Lys Gly Ala Ala Gly Pro Leu Pro Ser Glu Ala Val Gln Trp
            1060                1065                1070

Leu Cys His Gln Ala Phe Leu Leu Lys Leu Thr Arg His Arg Val Thr
    1075                1080                1085

Tyr Val Pro Leu Leu Gly Ser Leu Arg Thr Ala Gln Thr Gln Leu Ser
    1090                1095                1100
```

```
Arg Lys Leu Pro Gly Thr Thr Leu Thr Ala Leu Glu Ala Ala Ala Asn
1105                 1110                1115                1120

Pro Ala Leu Pro Ser Asp Phe Lys Thr Ile Leu Asp
                1125                1130
```

```
<210> SEQ ID NO 3
<211> LENGTH: 6
<212> TYPE: PRT
<213> ORGANISM: Homo sapiens
<220> FEATURE:
<221> NAME/KEY: PEPTIDE
<222> LOCATION: (1)..(6)
<223> OTHER INFORMATION: amino acid positions 560-565 from
      hTRT

<400> SEQUENCE: 3

Phe Phe Tyr Val Thr Glu
  1               5

<210> SEQ ID NO 4
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: amino acid positions 405-418 from
      hTRT

<400> SEQUENCE: 4

Tyr Gly Val Leu Leu Lys Thr His Cys Pro Leu Arg Ala Ala
  1               5                  10

<210> SEQ ID NO 5
<211> LENGTH: 4
<212> TYPE: PRT
<213> ORGANISM: Homo sapiens
<220> FEATURE:
<221> NAME/KEY: PEPTIDE
<222> LOCATION: (1)..(4)
<223> OTHER INFORMATION: amino acid positions 561-564 from
      hTRT

<400> SEQUENCE: 5

Phe Tyr Val Thr
  1

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:RT1 oligo

<400> SEQUENCE: 6
gaaggccgcc cacgggcacg tccgc                                        25

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:RT2 oligo

<400> SEQUENCE: 7
cccggccacc ccagccatgg cgcgcgctcc cc                                32
```

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence:RT5 oligo

<400> SEQUENCE: 8
tacggggtgc tcctcaagac gcactgcccg ctgctccgcc agcacagcag ccectggcag     60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence:RT10 oligo

<400> SEQUENCE: 9
tactccatcc tgaaagccaa gaacgcaggg ctgtgccacc aagcattcct gctcaagctg     60

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence:RT11 oligo

<400> SEQUENCE: 10
ctgtgccacc aagcattcct gctcaagctg gccgcagcca acccggcact gccctcagac     60

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence:RT3A oligo

<400> SEQUENCE: 11
actcaggccc ggcccccgcc acacgctagc gagaccaagc acttcctcta ctcctcaggc     60

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence:RT4A oligo

<400> SEQUENCE: 12
actcaggccc ggcccccgcc acacgctagc gtggtgtcac ctgccagacc cgccgaagaa     60

<210> SEQ ID NO 13
<211> LENGTH: 69
<212> TYPE: DNA
<213> ORGANISM: Artificial Sequence
<220> FEATURE:
<223> OTHER INFORMATION: Description of Artificial Sequence:RT6A oligo

<400> SEQUENCE: 13
atccccaagc ctgacgggct gcggccgatt gttaacatgc tgttcagcgt gctcaactac     60
gagcgggcg                                                            69

```
<210> SEQ ID NO 14
<211> LENGTH: 63
<212> TYPE: DNA
<213> ORGANISM: Artificial Sequence
<220> FEATURE:
<223> OTHER INFORMATION: Description of Artificial Sequence:RT8A oligo

<400> SEQUENCE: 14
acgtactgcg tgcgtcggta tgccgtggtc acagatctcc agccgtacat gcgacagttc      60
gtg                                                                   63

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence:RT3A/5 oligo

<400> SEQUENCE: 15
actcaggccc ggcccccgcc acacgctagc ctgctccgcc agcacagcag ccctggcag       60

<210> SEQ ID NO 16
<211> LENGTH: 63
<212> TYPE: DNA
<213> ORGANISM: Artificial Sequence
<220> FEATURE:
<223> OTHER INFORMATION: Description of Artificial Sequence:LM121-WG
      oligo

<400> SEQUENCE: 16
gttcagatgc cggcccacgg cctattccct ctagataccc ggaccctgga ggtgcagagc      60
gac                                                                   63

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence:LM122-Nuc
      oligo

<400> SEQUENCE: 17
ccctgggcct gccagccccg ggtgccggcg ctgcccctga gccggagcgg                 50

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence:RT3 oligo

<400> SEQUENCE: 18
gctagtggac cccgaaggcg tctgggatgc gagaccaagc acttcctcta ctcctcaggc      60

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence:RT4 oligo

<400> SEQUENCE: 19
gctagtggac cccgaaggcg tctgggatgc gtggtgtcac ctgccagacc cgccgaagaa      60
```

```
<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence:RT6 oligo

<400> SEQUENCE: 20
gacgggctgc ggccgattgt gaacatggac ctgttcagcg tgctcaacta cgagcgggcg     60

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence:RT8 oligo

<400> SEQUENCE: 21
acgtactgcg tgcgtcggta tgccgtggtc accttgacag acctccagcc gtacatgcga     60
```

INACTIVE VARIANTS OF THE HUMAN TELOMERASE CATALYTIC SUBUNIT

CROSS-REFERENCE TO RELATED APPLICATIONS

This application is a continuation of U.S. patent application Ser. No. 09/128,354, filed Aug. 3, 1998, now U.S. Pat. No. 6,337,200; which is a continuation-in-part of U.S. patent application Ser. No. 09/052,864, filed Mar. 31, 1998, now abandoned.

The aforellsted priority applications are hereby incorporated herein by reference in their entirety, as are the following: U.S. patent application Ser. Nos. 08/851,843; 08/854,050; 08/911,312; 08/912,951; 08/915,503; 08/974,548; and 08/974,584; and international Patent Publications WO 98/14592 and WO 98/14593.

FIELD

The present invention is related to the catalytic protein subunit of human telomerase. The invention provides methods and compositions relating to medicine, molecular biology, chemistry, pharmacology, and medical diagnostic and prognostic technology.

BACKGROUND

The following discussion is intended to introduce the field of the present invention to the reader. The citation of various references in this section should not be construed as an admission of prior invention.

It has long been recognized that complete replication of the ends of eukaryotic chromosomes requires specialized cell components (Watson, 1972, *Nature New Biol.*, 239:197; Olovnikov, 1973, *J. Theor. Biol,* 41:181). Replication of a linear DNA strand by conventional DNA polymerase requires an RNA primer, and can proceed only 5 to 3'. When the RNA bound at the extreme 5' ends of eukaryotic chromosomal DNA strands is removed, a gap is introduced, leading to a progressive shortening of daughter strands with each round of replication. This shortening of telomeres, the protein-DNA structures physically located on the ends of chromosomes, is thought to account for the phenomenon of cellular senescence or aging of normal human somatic cells in vitro and in vivo. The maintenance of telomeres is a function of a telomere-specific DNA polymerase known as telomerase. Telomerase is a ribonucleoprotein (RNP) that uses a portion of its RNA moiety as a template for telomeric DNA synthesis (Morin, 1997, *Eur. J. Cancer* 33:750). The length and integrity of telomeres and the telomerase expression status of a cell is thus related to entry of a cell into a senescent stage (i.e., loss of proliferative capacity), or the ability of a cell to escape senescence, i.e., to become immortal.

Consistent with the relationship of telomeres and telomerase to the proliferative capacity of a cell (i.e., the ability of the cell to divide indefinitely), telomerase activity is detected in Immortal cell lines and an extraordinarily diverse set of tumor tissues, but is not detected (i.e., was absent or below the assay threshold) in normal somatic cell cultures or normal tissues adjacent to a tumor (see, U.S. Pat. Nos. 5,629,154; 5,489,508; 5,648,215; and 5,639,613; see also, Morin, 1989, *Cell* 59: 521; Shay and Bacchetti 1997, *Eur. J. Cancer* 33:787; Kim et al., 1994, *Science* 266:2011; Counter et al., 1992, *EMBO J.* 11:1921; Counter et al., 1994, *Proc. Natl. Acad. Sci. U.S.A.* 91, 2900; Counter et al., 1994, *J. Virol.* 688:3410). Moreover, a correlation between the level of telomerase activity in a tumor and the likely clinical outcome of the patient has been reported (e.g., U.S. Pat. No. 5,639,613, supra; Langford et al., 1997, *Hum. Pathol.* 28:416). Thus, human telomerase is an ideal target for diagnosing and treating human diseases relating to cellular proliferation and senescence, such as cancer, or for increasing the proliferative capacity of a cell.

SUMMARY

In one aspect, the invention provides an isolated or recombinant hTRT polypeptide that has telomerase catalytic activity. In one embodiment, the hTRT polypeptide has a deletion of at least 25 residues in the regions corresponding to residues 192–323, 200–323, 192–271, 200–271, 222–240, 415–450, 192–323 and 415–450, or 192–271 and 415–450 of hTRT. In a related embodiment, residues 192–323, 200–323, 192–271, 200–271, 222–240, 415–450, 192–323 and 415–450, or 192–271 and 415–450 of hTRT are deleted. The invention also provides a polynucleotide comprising a nucleotide sequence encoding these hTRT polypeptides. In some embodiments, the polynucleotide includes a promoter sequence operably linked to the nucleotide sequence encoding the hTRT polypeptide.

The invention also provides a method of preparing recombinant telomerase by contacting a recombinant hTRT polypeptide containing a deletion as described supra with a telomerase RNA component under conditions such that the recombinant protein and the telomerase RNA component associate to form a telomerase enzyme capable of catalyzing the addition of nucleotides to a telomerase substrate. The hTRT polypeptide may be produced in an in vitro expression system and/or may be purified before the contacting step. In some embodiments, the contacting occurs in a cell.

The invention further provides a method for increasing the proliferative capacity of a vertebrate cell by introducing into a cell the recombinant hTRT polynucleotide encoding an hTRT deletion variant described supra. In a related embodiment, the invention provides a cell, such as a human cell or other mammalian call, comprising a nucleotide sequence that encodes the hTRT deletion variant polypeptide. The invention provides such cells that have an increased proliferative capacity relative to a cell that is otherwise identical but does not comprise the recombinant polynucleotide.

In a different aspect of the invention, an isolated or recombinant hTRT polypeptide that has a deletion of amino acid residues 192–450, 560–565, 637–660, 748–766, 748–764, or 1055–1071, where the residue numbering is with reference to the hTRT polypeptide having the sequence provided in FIG. 1, is provided. In one embodiment, the hTRT protein fragment has at least 6 amino acid residues. In other embodiments, the hTRT protein fragment has at least 8, at least about 10, at least about 12, at least about 15 or at least about 20 contiguous amino acid residues of a naturally occurring hTRT polypeptide. In still other embodiments, the hTRT protein fragment has at least about 50 or at least about 100 amino acid residues. In a related aspect, the invention provides an isolated, recombinant, or substantially purified polynucleotide encoding this polypeptide, which in some embodiments includes a promoter sequence operably linked to the nucleotide sequence encoding the hTRT polypeptide.

The invention also provides a method of reducing telomerase activity in a cell by introducing the polynucleotide described supra (i.e., having a deletion of amino acid residues 192–450, 560–565, 637–660, 638–660, 748–766, 748–764, or 1055–1071) into a cell under conditions in which it is expressed.

In a related embodiment, the hTRT polypeptide has one or more mutations other than, or in addition to, a deletion of at least 25 residues in the regions corresponding to residues 192–323, 200–323, 192–271, 200–271, 222–240, 415–450, 192–323 and 415–450, or 192–271 and 415–450 of hTRT.

DRAWINGS

FIG. 1 shows the amino acid sequence of a 1132-residue human telomerase reverse transcriptase (hTRT) protein (SEQ. ID NO:2).

FIG. 2 shows the nucleotide sequence of a naturally occurring cDNA encoding the hTRT protein (SEQ. ID NO:1).

DETAILED DESCRIPTION

I. Introduction

Telomerase is a ribonucleoprotein complex (RNP) comprising an RNA component and a catalytic protein component. The catalytic protein component of human telomerase, hereinafter referred to as telomerase reverse transcriptase ("hTRT"), has been cloned, and protein, cDNA and genomic sequences determined. See, e.g., Nakamura et al., 1997, Science 277:955, and U.S. Pat. Nos. 6,475,789 and 6,166,178. The sequence of a full-length native hTRT has been deposited in GenBank (Accession No. AF015950), and plasmid and phage vectors having hTRT coding sequences have been deposited with the American Type Culture Collection, Rockville, Md. (accession numbers 209024, 209016, and 98505). The catalytic subunit protein of human telomerase has also been referred to as "hEST2" (Meyerson et al. 1997, Cell 90:785), "hTCS1" (Kilian et al., 1997, Hum. Mol. Genet. 6:2011), "TP2"(Harrington et al., 1997, Genes Dev. 11:3109), and "hTERT" (e.g., Greider, 1998, Curr. Biol 8: R178–R181). Human TRT is also described in the aforereferenced priority applications and U.S. patent application Ser. Nos. 08/846,017, 08/844,419, and 08/724,643. The RNA component of human telomerase (hTR) has also been characterized (see U.S. Pat. No. 5,583,016). All of the aforementioned applications and publications are incorporated by reference herein in their entirety and for all purposes.

Human TRT is of extraordinary interest and value because, inter alia, telomerase activity in human cells and other mammalian cells correlates with cell proliferative capacity, cell immortality, and the development of a neoplastic phenotype. Thus, hTRT polypeptides, including the hTRT variants described herein, and polynucleotides encoding hTRT polypeptides, are used, inter alia for conferring a telomerase activity (e.g., telomerase catalytic activity, infra) in a telomerase negative cell such as a cell from a human, a mammal, a vertebrate, or other eukaryote (see, e.g., Bodnar et al., 1998, Science 279:349 and U.S. Pat. Nos. 6,475,789 and 6,166,178). Variants that lack at least one hTRT activity (e.g., telomerase catalytic activity) are used, inter alia, to inhibit telomerase activity in a cell (e.g. by acting as "dominant negative mutants"). The hTRT variants and polynucleotides encoding them, as described herein, are similarly useful in screening assays for identifying agents that modulate telomerase activity.

The hTRT variants of the present invention are characterized by one or more deletions or mutations, relative to a naturally occurring hTRT polypeptide, in defined regions of the protein, as described in detail infra. These hTRT variants may have none, one, or several of the biological activities that may be found in naturally occurring full-length hTRT proteins. These activities include telomerase catalytic activity (the ability to extend a DNA primer that functions as a telomerase substrate by adding a partial, one, or more than one repeat of a sequence, e.g., TTAGGG, encoded by a template nucleic acid, e.g., hTR), telomerase conventional reverse transcriptase activity (see Morin, 1997, supra, and Spence et al., 1995, Science 267–988; nucleolytic activity (see Morin, 1997, supra; Collins and Grieder, 1993, Genes and Development 7;1364; Joyce and Steitz, 1987, Trends Biochem. Sci. 12:288); primer (telomere) binding activity (see, Morin, 1997, supra; Collins et al., 1995, Cell 84:677; Harrington et al., 1995, J. Biol. Chem. 270:8893; dNTP binding activity (Morin, 1997, supra; Spence et al., supra); and RNA (e.g., hTRT) binding activity (see Morin, 1997, supra; Harrington et al., 1997, Science 275:973; Collins et. al., 1995. Cell 81:677).

In one embodiment of the invention, the hTRT variant has telomerase catalytic activity. Telomerase catalytic activity may be processive or nonprocessive. Processive telomerase catalytic activity occurs when a telomerase RNP adds multiple repeats to a primer or telomerase before, the DNA is released by the enzyme complex (see, e.g., Morin, 1989, Cell 59:521 and Morin, 1997, Eur. J. Cancer 33:750). Nonprocessive activity occurs when telomerase adds a partial, or only one, repeat to a primer and is then released (see Morin, 1997, supra). In a particular embodiment of the invention, the hTRT variant has processive telomerase catalytic activity.

Processive telomerase catalytic activity can be assayed by a variety of methods, including the "conventional assay" (Morin, 1989, Cell 59;521), the TRAP assay (U.S. Pat. No. 5,829,154; see also, PCT publication WO 97/15687, PCT publication WO 95,13381; Krupp et al. Nucleic Acids Res., 1997, 25: 919; Wright et al., 1995, Nucl. Acids Res. 23:3794), the "dot blot immunoassay" (U.S. patent application Ser. No. 08/833,377), and other assays (e.g., Tatematsu et al., 1996, Oncogene 13:2265). The TRAPeze™ Kit (Oncor, Inc., Gaithersburg, Md.) may be used. The telomerase substrate used in these assays may have a natural telomere sequence, or may be have a synthetic oligonucleotide with a different sequence (see, e.g., Morin, 1989, Cell 59:521: Morin, 1991, Nature 353:454–56).

As used herein, an hTRT variant is considered to have a specified activity if the activity is exhibited by either the hTRT variant polypeptide without an associated hTRT RNA or in an hTRT-hTR complex. Each of the hTRT activities described supra is also described in detail in U.S. Pat. Nos. 6,475,789 and 6,166,178.

II. hTRT Variants Described a) hTRT Variants With Telomerase Catalytic Activity

It has now been demonstrated that large regions of the hTRT protein can be mutated (e.g., deleted) without loss of telomerase catalytic activity. Sites of mutation (e.g., deletion) are described herein with reference to the amino acid sequence provided in FIG. 1 and encoded in plasmid pGRN121 (ATCC accession number 209016); however it will be recognized that the same or equivalent mutations may be made in other hTRT polypeptides, e.g., naturally occurring variants such as polymorphic variants, hTRT fusion proteins, hTRT homologs (e.g., from non-human species), and the like. For ease of discussion, the residues of the full-length hTRT protein having a sequence as provided in FIG. 1 are referred to herein by number, with the amino-terminal methionine (M) in FIG. 1 numbered "1", and the carboxy-terminal aspartic acid (D) numbered a "1132".

Regions of the hTRT protein that can be mutated (e.g., deleted) without abolishing telomerase catalytic activity include the regions from amino acid residues 192 to 323 (inclusive) and residues 415 to 450 (inclusive). As is demonstrated in the experiments described infra, all or part of either of these regions, or all or part of both of them can be deleted without abolishing the telomerase catalytic activity of the protein. The regions from amino acid residues 192 to 323 and residues 415 to 450 may be referred to as "nonessential" regions of hTRT (i.e., not essential for telomerase catalytic activity). Thus, in various embodiments, the hTRT variants of the invention comprise deletions of, or other mutations in, these nonessential regions of hTRT. As described in Section IV, infra, certain mutations (e.g., deletion of residues 415-450) alter RNA-binding characteristics of the hTRT variant.

Examples of mutations that can be made in the hTRT polypeptides of the invention include deletions, insertions, substitutions, and combination of mutations. Thus, in some embodiments the mutation is a deletion of at least one, typically at least about 10, and often at least about 25, at least about 50, or at least about 100 amino acid residues relative to a naturally occurring hTRT. In alternative embodiments, the mutation is a single amino acid substitution in a "nonessential" region or a combinations of substitutions substitutions may be conservative substitutions or non-conservative substitutions. In still other embodiments, the mutation is an insertion or substitution of amino acids, for example the insertion of residues that encode an epitope tag or novel proteolytic site. Substitutions may be of one or more (e.g., all) of the residues in the above-mentioned regions or may be combined with deletions so that, e.g., a shorter heterologous sequence is a substituted for a longer hTRT sequence. It will be appreciated, as noted supra, that in some embodiments the hTRT variant has more than one different type of mutation relative to a naturally occurring hTRT protein (e.g., a deletion and a point mutation).

The hTRT variants of the invention have certain advantages compared to naturally occurring hTRT proteins. In some embodiments, mutations may confer more efficient in vitro expression of active hTRT (e.g., in expression systems in which shorter polypeptides are more efficiently expressed than longer polypeptides), may provide sequences that aid in purification (e.g., an epitope tag sequence), or may add a new functional moiety to the hTRT polypeptide (e.g., a 3'→5' exonuclease domain from DNA polymerase 1).

As noted supra, the hTRT variant polypeptides of the invention comprising mutations (e.g., deletions) in the "nonessential" regions of the hTRT retain telomerase catalytic activity. These variants, and polynucleotides that encode them, are useful in any application for which other catalytically active hTRT proteins (e.g., wild-type hTRT proteins) or polynucleotides may be used, including, inter alia, in therapeutic, diagnostic, and screening uses. Exemplary uses of hTRT polypeptides and polynucleotides are described in additional detail in the afore cited U.S. Pat. Nos. 6,475,789 and 6,166,178.

In one embodiment, the hTRT variant of the invention is used to increase the proliferative capacity of a cell by, e.g., increasing telomerase activity in the cell (see, Bodnar et al. supra, and U.S. Pat. Nos. 6,475,789 and 6,166,178 for a detailed description of exemplary methods). Briefly, in one embodiment, a polynucleotide comprising (i) a sequence encoding the hTRT variant polypeptide; (ii) an operably linked promoter (e.g., a heterologous promoter); and, (iii) optionally polyadenylation and termination signals, enhancers, or other regulatory elements, is introduced into a target cell (e.g., by transfection, lipofection, electroporation, or any other suitable method) under conditions in which the hTRT variant polypeptide is expressed. The expression in the cell of the catalytically active hTRT variant of the invention results in increased proliferative capacity (e.g., an immortal phenotype).

In another embodiment, the hTRT variant is used for in vitro reconstitution (IVR) of a telomerase ribonucleoprotein (e.g., comprising the HTRT variant polypeptide and a template RNA, e.g., hTR) that has telomerase catalytic activity. In vitro reconstitution methods are described in, e.g., Weinrich et al., 1997, Nat Genet. 17:498, and U.S. Pat. Nos. 6,475,789 and 6,166,178. Briefly, in one embodiment, an expression vector encoding an hTRT variant of the invention is expressed in an in vitro expression system (e.g., a coupled transcription-translation reticulocyte lysate system such as that described in U.S. Pat. No. 5,324,637). In a particular embodiment, the hTRT variant polypeptide is coexpressed with hTR. In an alternative embodiment, the hTRT variant and hTR are separately expressed and then combined (mixed) in vitro. In the latter method, the hTR RNA and/or hTRT polypeptide may be purified before mixing. In this context, the hTRT polypeptide is 'purified' when it is separated from at least one other component of the in vitro expression system, and it may be purified to homogeneity as determined by standard methods (e.g., SDS-PAGE). The in vitro reconstituted (IVR) telomerase has a variety of uses, in particular it is useful for identifying agents that modulate hTRT activity (e.g., drug screening assays).

(b) Deletion Variants Lacking Telomerase Catalytic Activity

In an other aspect, the invention provides hTRT deletion variants that lack telomerase catalytic activity (i.e., having less than 1% of the wild type activity), as well as polynucleotides encoding the variants lacking telomerase catalytic activity. In particular, the invention provides variants comprising one or more of the following deletions relative to wild-type hTRT: residues 192–450, 637–660, 638–460, 748–768, 748–764, and 1055–1071. These variants are referred to herein as PCA$^-$ variants (processive telomerase catalytic activity minus variants).

The PCA$^-$ variant proteins and polynucleotides of the invention lacking telomerase catalytic activity are used in, inter alia, therapeutic, screening and other applications. For example, PCA– variants are useful as dominant negative mutants for inhibition of telomerase activity in a cell. In one embodiment, a PCA$^-$ variant is introduced into a cell (e.g., by transfection with a polynucleotide expression vector expressing the PCA$^-$ variant), resulting in sequestration of a cell component (e.g., hTR) required for accurate telomere elongation. Thus, for example, administration of a polypeptide that binds hTR, a DNA primer, a telomerase-associated protein, or other cell component, but which does not have telomerase catalytic activity, is used to reduce endogenous telomerase activity in the cell or to otherwise interfere with telomere extension (e.g., by displacing active telomerase from telomeric DNA). Similarly, in certain embodiments, a PCA$^-$ variant of the invention having one- or several hTRT activities (i.e. other than processive telomerase catalytic activity) is used for screening for agents that specifically modulate (inhibit or activate) a telomerase activity other than telomerase catalytic activity. The use of hTRT variants as dominant negative mutants and in other applications. Is described in detail in U.S. Pat. Nos. 6,475,789 and 6,166,178.

III. Making hTRT Variants

The hTRT variant polypeptides and polynucleotides of the invention may be produced using any of a variety of techniques known in the art. In one embodiment, a polypeptide having the desired sequence, or a polynucleotide encoding the polypeptide, is chemically synthesized (see, e.g., Roberge, et al., 1995, *Science* 269:202; Brown et al., 1979, *Meth. Enzymol* 68:109). More often, the hTRT variant polypeptides and polynucleotides of the invention are created by manipulation of a recombinant polynucleotide encoding an hTRT polypeptide. Examples of suitable recombinant polynucleotides include pGRN121, supra, and other hTRT cDNA and gonomic sequences.

Methods for cloning and manipulation of hTRT encoding nucleic acids (e.g., site-specific mutagenesis, linker scanning mutagenesis, and the like) are well known in the art and are described, for example, in Sambrook et al., 1989, MOLECULAR CLONING: A LABORATORY MANUAL. 2ND ED., VOLS. 1–3. Cold Spring Harbor Laboratory, and Ausubel et al. 1997, CURRENT PROTOCOLS IN MOLECULAR BIOLOGY, Greene Publishing and Wiley-Interscience, New York. One convenient method for producing a polynucleotide encoding a desired hTRT deletion variant is by restriction digestion and subsequent ligation of a hTRT polynucleotide, to remove a region(s) of the polynucleotide encoding the amino acid residues to be deleted. If desired, restriction sites can be introduced or removed from a synthetic or naturally occurring hTRT gone to facilitate the production and detection of variants.

Typically, the recombinant polynucleotide encoding an hTRT variant of the invention is linked to appropriate regulatory elements (e.g., promoters, enhancers, polyadenylation signals, and the like) and expressed in a cell free system (see, e.g. Weinrich et al., supra), in bacteria (e.g., *E. coli*). In ex vivo animal cell culture (see, e.g., Bodnar et al., supra), in animals or plants (e.g., transgenic organisms or in gone therapy applications), or by any other suitable method. Suitable expression systems are well known in the art and include those described in Weinrich et al., and Bodnar et al., both supra, and in U.S. Pat. Nos. 6,475,789 and 6,166,178.

U.S. Pat. No. 6,166,178 refers to methods, regents, vectors, and cells useful for expression of hTRT polypeptides and nucleic acids. In on embodiment, expression of the hTRT protein, or fragment thereof, comprises inserting the coding sequence into an appropriate expression vector (i.e., a vector that contains the necessary elements for the transcription and translation of the inserted coding sequence required for the expression system employed). For mammalian host cells, viral-based and nonviral expression systems are provided. Nonviral vectors and systems include plasmids and episomal vectors. Useful viral vectors include vectors based on retroviruses, adenoviruses, adeno-associated viruses, herpes viruses, vectors based on SV40, papilloma virus, HBP Epstein Barr viruses, vaccinia virus vectors and Semliki Forest virus (SFV).

For the production of anti-hTRT antibodies, hosts such as goats, sheep, cows, guinea pigs, rabbits, rats, or mice, may be immunized by injection with hTRT protein or any portion fragment, or oligopeptide thereof that retains immunogenic properties. In selecting hTRT polypeptides for antibody induction, one need not retain biological activity; however, the protein fragment, or oligopeptide must be immunogenic. Immunogenicity can be determined by injecting a polypeptide and adjuvant into an animal (e.g., a rabbit) an assaying for the appearance of antibodies directed against the injected polypeptide (Harlow and Lane, *Antibodies: A laboratory Manual*, Cold Spring Harbor Laboratory, New York, 1988).

Peptides used to induce specific antibodies typically have an amino acid sequence consisting of at least five amino acids, preferably at least 8 amino acids, more preferably at least 10 amino acids. Usually they will mimic or have substantial sequence identity to all or contiguous portion of the amino acid sequence of the protein of SEQ ID, NO:2. Depending on the host species, various adjuvante may be used to increase immunological response. Immunogenic peptides or polypeptides having an hTRT sequence can be used to elicit an anti-hTRT immune response in a patient (i.e., act as a vaccine). An immune response can also be raised by delivery of plasmid vectors encoding the polypeptide of interest. Further details on techniques for formulation and administration may be found in the latest edition of *Remington's Pharmaceutical Sciences*, Maack Publishing Co., Easton Pa.

Additional hTRT variants of the invention may be made using "DNA shuffling" in vitro recombination technology (see, e.g., Crameri et al., 1998, *Nature* 391:288–291; Panen at al., 1997, *Curr. Opin. Biotechnol.* 8:724–733, Stemmer, 1994, *Nature* 370:389–391; Crameri et al., 1996, *Nature Medicine*, 2:1–3: Crameri at al., 1996, *Nature Biotechnology* 14:315–319; WO 95/22625; Stemmer, 1995, *Science* 270: 1510; Stemmer et al., 1995, *Gene*, 164, 49–53; Stemmer, 1995, *Bio/Technology*, 13:549–553; Stemmer, 1994, *Proc. Natl. Acad. Sci. USA* 91:10747–10751). The specific deletion variants described supra, "wild-type hTRT" and non-human hTRT-homologs may be used in individually or various combinations as starting substrates to produce novel polypeptides with the desired activity. The activity or activities of the resulting polypeptides determined using the assays described in Section I, supra.

IV. Exemplary hTRT Variants a) Generally

Exemplary hTRT variants were created by in vitro mutagenesis of polynucleotides encoding a full-length hTRT protein using the method of Perez et al. 1994, *J. Biol. Chem.* 269:22485–87. The mutant polynucleotides were expressed in vitro and telomerase reconstituted by in vitro mixing of hTRT and human telomerase RNA as described in Weinrich et al., 1997, supra. Reconstitution reactions were carried out using 0.5 pmole, 20 pmole, and, in some cases, other amounts of added hTR. Telomerase processive catalytic activity was assayed using a modified TRAP assay (Weinrich et al., 1997, supra). The results are summarized in Table 1.

TABLE 1

| Deletion Name | Oligo | Amino acids deleted | Activity[1] |
|---|---|---|---|
| pGRN234 | RT1 + RT2 | none (delete Ncol site) | + |
| pGRN226 | RT3A | 192–323 | + |
| RT3 | RT3 | 200–326 | + |
| pGRN237 | RT4A | 192–271 | + |
| RT4 | RT4 | 200–271 | + |
| pGRN210 | LM122-Nuc | 222–240 | + |
| pGRN235 | RT5 | 415–450 | + |
| pGRN242 | RT3A + RT5 | 192–326 + 415–450 | + |
| pGRN243 | RT4A + RT5 | 192–271 + 415–450 | + |
| pGRN240 | RT3A/5 | 192–450 | − |
| pGRN238 | RT6A | 637–660 | − |
| RT6 | RT 6 | 638–660 | − |
| pGRN239 | RT8A | 748–766 | − |

TABLE 1-continued

| Deletion Name | Oligo | Amino acids deleted | Activity[1] |
|---|---|---|---|
| RT8 | RT8 | 748–764 | – |
| pGRN241 | RT10 | 1055–1071 | – |
| pGRN236 | RT11 | 1084–1116 | – |
| pGRN209 | LM121-WG | 930–934 | – |
| pGRN231 | | 560–565 | – |

"+" = at least 40% activity compared to in vitro reconstitution using wild-type hTRT (e.g., encoded by pGRN125; see Weinrich et al., 1997, supra)
"–" = less than 1% activity.

Certain of the hTRT variants described supra are altered in their ability to bind hTR. The variants encoded by pGRN235, pGRN242 and pGRN243 exhibited telomerase activity when 20 pmoles hTR (template RNA) was included in the reconstitution reaction, but showed a low or undetectable level of activity when 0.5 pmoles of hTR was used. The variable activity of these variants indicates that these variants have altered (e.g., decreased) hTR binding activity. Thus, the region from 415 to 450 is likely involved in RNA binding (e.g., by affecting the conformation of the protein).

This result suggests that the region immediately upstream of residue 415, corresponding to the conserved "CP" domain (Bryan et al., 1998, Proc. Natl. Acad. Sci. 95:8479–8484) is a region of contact between the hTRT protein and hTR (e.g., corresponding to about residues 405 to 418 as set forth in FIG. 1). This conclusion is supported by the relative lack of conservation of sequence when human and mouse TRT sequences are compared in the region corresponding to hTRT residues 415–450.

hTR binding to hTRT was also affected by mutations and deletions in the region 560–565. RNA binding was assayed by adding purified hTR to epitope tagged TRT proteins (i.e., including a FLAG sequence; Immunex Corp. Seattle Wash.). The hTR and protein were incubated under conditions under which tagged wild-type hTRT associates with template RNA (hTR), and the hTRT protein or hTRT-hTR complex (it present) were immunoprecipitated. The precipitated complex was assayed for the presence and amount of associated RNA. Deletion of residues 560–565 dramatically decreased the binding of hTR by hTRT, with the concurrent expected decrease in telomerase activity (see Table 1, pGRN231). Mutation of phenylalanine (F) to alanine (A) mutation at position 561 of hTRT (the "F561A" variant; see. Weinrich et al., 1997, supra) resulted in reduced binding of hTR; this variant did not effectively bind hTR in association reactions when hTR was present at 0.5 pmoles, and showed less-than wild-type binding at 20 pmoles hTR. Mutation of tyrosine at 562 to alanine similarly resulted in a loss of hTR binding activity (e.g., about a 70–80% reduction compared to the wild-type sequence). Mutation of threonine at position 564 to alanine the resulted in a decrease in RNA binding by approximately 20% compared to wild-type. In contrast, mutation of residues 560 (F) and 565 (E) to alanine did not affect hTR binding. These results indicate that the region from 560–565 is involved in RNA binding, e.g., by providing residues that Contact hTR.

As will be apparent to one of skill advised of these results, the telomerase reconstitution may be inhibited using peptides comprising the sequence corresponding the hTRT residues 405–418, 560–565, or fragments thereof, or peptide mimetics of such sequences. Thus, in one embodiment of the present invention, telomerase activity in a cell or an in vitro composition in which TRT protein and TR RNA are present, such as a telomerase reconstitution assay, is reduced by introducing to the cell or in vitro composition a polypeptide comprising the sequence FFYVTE (SEQ. ID NO:3), a polypeptide comprising the sequence YGVLLKTHCPLRAA (SEQ. ID NO:4), a polypeptide consisting essentially of FFYVTE (SEQ. ID NO: 3), a polypeptide consisting essentially of FYVT(SEQ. ID NO:5), a polypeptide consisting essentially of YGVLLKTHCPLRAA (SEQ. ID NO:4), a fragment of at least three residues of the aforementioned polypeptides, or a peptide analog or mimetic of the polypeptide of any of the aforementioned compositions.

Peptide mimetics (or peptide analogs) are well known and are commonly used in the pharmaceutical industry as non-peptide drugs with properties analogous to those of the template polypeptide (Fauchere, 1986, Adv. Drug Res. 15:29; Veber et al., 1985, TINS p. 392; and Evans et al., 1987, J. Med. Chem. 30:1229). Generally, peptidomimetics are structurally similar to the paradigm polypeptide having the sequence from hTRT but have one or more peptide linkages optionally replaced by a linkage selected from the group consisting of: $-CH_2NH-$, $-CH_2S-$, $-CH_2-CH_2-$, $-CH'CH-$ (cis and trans), $-COCH_2-$, $-CH(OH)CH_2-$, and $-CH_2SO-$. Peptide mimetics may have significant advantages over polypeptide embodiments of this invention, including, for example: more economical production, greater chemical stability, enhanced pharmacological properties (half-life, absorption, potency, efficacy, etc.), altered specificity (e.g., a broad-spectrum of biological activities), reduced antigenicity, and others. In addition to modifications to the peptide backbone, synthetic or non-naturally occurring amino acids can also be used to substitute for the amino acids present in the polypeptide or in the functional moiety of fusion proteins. Synthetic or non-naturally occurring amino acids refer to amino acids which do not naturally occur in vivo but which, nevertheless, can be incorporated into the peptide structures described herein. Preferred synthetic amino acids are the d-α-amino acids of naturally occurring i-α-amino acid, mentioned above, as well as non-naturally occurring d- and i-α-amino acids represented by the formula H2NCHR5COOH where R5 is 1) a lower alkyl group, 2) a cycloalkyl group of from 3 to 7 carbon atoms, 3) a heterocycle of from 3 to 7 carbon atoms and 1 to 2 heteroatoms selected from the group consisting of oxygen, sulfur, and nitrogen, 4) an aromatic residue of from 6 to 10 carbon atoms optionally having from 1 to 3 substituents on the aromatic nucleus selected from the group consisting of hydroxyl, lower alkoxy, amino, and carboxyl, 5)-alkylene-Y where alkylene is an alkylene group of from 1 to 7 carbon atoms and Y is selected from the group consisting of (a) hydroxy, (b) amino, (a) cycloalkyl and cycloalkenyl of from 3 to 7 carbon atoms, (d) aryl of from 6 to 10 carbon atoms optionally having from 1 to 3 substituents on the aromatic nucleus selected from the group consisting of hydroxyl, lower alkoxy, amino and carboxyl, (a) heterocyclic of from 3 to 7 carbon atoms and 1 to 2 heteroatoms selected from the group consisting of oxygen, sulfur, and nitrogen, (f) $-C(O)R2$ where R2 is selected from the group consisting of hydrogen, hydroxy, lower alkyl, lower alkoxy, and $-NR3R4$ where R3 and R4 are independently selected from the group consisting of hydrogen and lower alkyl, (g) $-S(O)nR6$ where n is an integer from 1 to 2 and R6 is lower alkyl and with the proviso that R5 does not define a side chain of a naturally occurring amino acid. Other preferred synthetic amino acids include amino acids wherein the amino group is separated from the carboxyl group by more than one carbon atom such as β-alanine. γ-aminobutyric acid, and the like.

It will also be recognized by those of skill upon reviewing these results that the compositions (e.g., polypeptides and mimetics) described sugar can be used to identify telomerase association and activity inhibitors other than the disclosed CAT in the histidine residue at position 754) and introducing a new NcoI site at the translation start site (ATG). Table 2 shows exemplary oligonucleotides used to generate the plasmids expressing the deletion variants of the invention.

TABLE 2

| Oligo Name | Oligo sequence 5'-3' | length | Description | SEQ. ID NO: |
|---|---|---|---|---|
| RT1 | GAAGGCCGCCCACGGGCACGTCC GC | 25 | Mutagenesis oligo to delete Nco I site from pGRN125 | 6 |
| RT2 | CCCGGCCACCCCAGCCATGGCGC GCGCTCCCC | | Mutagenesis oligo to create Nco I site @ ATG of pGRN 125 | 7 |
| RT5 | TACGGGGTGCTCCTCAAGACGCAC TGCCCGCTGCTCCGCCAGCACAGC AGCCCCTGGCAG | 60 | Mutagenesis oligo to create a deletion of aa 415–450 in pGRN125 | 8 |
| RT10 | TACTCCATCCTGAAAGCCAAGAAC GCAGGGCTGTGCCACCAAGCATTC CTGCTCAAGCTG | 60 | Mutagenesis oligo to create a deletion of aa 1055–1071 in pGRN125 | 9 |
| RT11 | CTGTGCCACCAAGCATTCCTGCTC AAGCTGGCCGCAGCCAACCCGGC ACTGCCCTCAGAC | 60 | Mutagenesis oligo to create a deletion of aa 1083–1116 in pGRN125. Oligo creates a NheI site. | 10 |
| RT3A | ACTCAGGCCCGGCCCCCGCCACA CGCTAGCGAGACCAAGCACTTCCT CTACTCCTCAGGC | 60 | Mutagenesis oligo to create a deletion of aa 192–323 in pGRN125. Oligo creates a NheI site. | 11 |
| RT4A | ACTCAGGCCCGGCCCCCGCCACA CGCTAGCGTGGTGTCACCTGCCAG ACCCGCCGAAGAA | 60 | Mutagenesis oligo to create a deletion of aa 192–271 in pGRN125. Oligo creates a NheI site. | 12 |
| RT6A | ATCCCCAAGCCTGACGGGCTGCGG CCGATTGTTAACATGCTGTTCAGCG TGCTCAACTACGAGCGGGCG | 69 | Mutagenesis oligo to create a deletion of aa 638–660 in pGRN125. Oligo creates a Hpa I site. | 13 |
| RT8A | ACGTACTGCGTGCGTCGGTATGCC GTGGTCACAGATCTCCAGCCGTAC ATGCGACAGTTCGTG | 63 | Mutagenesis oligo to create a deletion of aa 748–766 in pGRN125. Oligo creates a Bgl II site. | 14 |
| RT3A/5 | ACTCAGGCCCGGCCCCCGCCACA CGCTAGCCTGCTCCGCCAGCACAG CAGCCCCTGGCAG | 60 | Mutagenesis oligo to create a deletion of aa 192–450 in pGRN125. Oligo creates a NheI site. | 15 |
| LM121-WG | GTTCAGATGCCGGCCCACGGCCTA TTCCCTCTAGATACCCGGACCCTG GAGGTGCAGAGCGAC | 63 | Mutagenesis oligo to delete aa 930–934. Oligo introduces a new XbaI site | 16 |
| LM122-Nuc | CCCTGGGCCTGCCAGCCCCGGGT GCCGGCGCTGCCCCTGAGCCGGA GCGG | 50 | Mutagenesis oligo to delete aa 222–240. Oligo introduces a new Nae I site | 17 |
| RT3 | GCTAGTGGACCCCGAAGGCGTCTG GGATGCGAGACCAAGCACTTCCTC TACTCCTCAGGC | 60 | Mutagenesis oligo to create a deletion of aa 200–323 in pGRN125 | 18 |
| RT4 | GCTAGTGGACCCCGAAGGCGTCTG GGATGCGTGGTGTCACCTGCCAGA CCCGCCGAAGAA | 60 | Mutagenesis oligo to create a deletion of aa 200–271 in pGRN125 | 19 |
| RT6 | GACGGGCTGCGGCCGATTGTGAAC ATGGACCTGTTCAGCGTGCTCAAC TACGAGCGGGCG | 60 | Mutagenesis oligo to create a deletion of aa 638–660 in pGRN125 | 20 |
| RT8 | ACGTACTGCGTGCGTCGGTATGCC GTGGTCACCTTGACAGACCTCCAG CCGTACATGCGA | 60 | Mutagenesis oligo to create a deletion of aa 748–764 in pGRN125 | 21 | polypeptide and mimetics. These compositions may be used, for example, in rational drug design for e.g., computer modeling of telomerase activity modulators (e.g., modulators that inhibit the association of TRT and TR or that catalyze the disassociation of the telomerase complex), as positive controls in screens for modulators of telomerase activity, or in competition assays with candidate telomerase activity modulators.

b) Methods

Mutagenesis of the hTRT coding sequence of pGRN125 was carried out using the methods described by Perez et al., 1994. *J. Biol. Chem.* 269:22485–87. Most of the deletion mutants were generated from the plasmid pGRN125 (Weinrich et al., 1997, supra). Deletion mutants pGRN235 and pGRN236 were made in a secondary round of mutagenesis in an altered pGRN234. pGRN234 was generated by mutating (deleting) the Nco I site in pGRN125 (changing CAC to V. Definitions The following terms are defined infra to provide additional guidance to one of skill in the practice of the invention:

When comparing regions between a first and second polypeptide, sequences can be aligned by inspection (e.g., alignment of identical sequences) or by computer implemented alignment of the two sequences.

Thus, for example, the residues 192 to 323 of the hTRT polypeptide having the sequence set forth in FIG. 1 "correspond" to residues in the same position in a hTRT polypeptide that differs from the FIG. 1 sequence due to polymorphic variation, or other mutations or deletions (e.g., when the two polypeptides are optimally aligned). Alignments may also be carried out using the GAP computer program, version 6.0 (Devereux et al, 1984. Nucl. Acid. Res. 12:387; available from the University of Wisconsin Genetics Computer Group. Madison, Wis.). The GAP program utilizes the alignment method of Needleham and Wunsch, 1970 J. Mol. Biol. 48: 443–453 as revised by Smith and Waterman, 1981, Adv. Appl. Math 2:482. The preferred default parameters for the GAP program include (1) the weighted comparison matrix of Gribskov and Burgess, 1988, Nucl. Acid. Res. 14:6745 as described by Schwartz and Dayhoff, eds., 1979, ATLAS OF PROTEIN SEQUENCE AND STRUCTURE, National Biomedical Research Foundation, pp. 353–458 (2) a penalty of 3.0 for each gap and an additional 0.10 penalty for each symbol in each gap; and (3) no penalty for end gaps. Alternatively, alignments can be carried out using the BLAST algorithm, which is described in Altschul et al., 1990, J. Mol. Biol. 215:403–410 using as defaults a wordlength (W) of 11, the BLOSUMS62 scoring matrix (see Henikoff & Henikoff, 1989, Proc. Natl. Acad. Sci. USA 89:10915); alignments (B) of 50, expectation (E) of 10, M=5, and N=4. A modification of BLAST, the "Gapped BLAST" allows gaps to be introduced into the alignments that are returned (Altschul et al., 1997, Nucleic Acids Res 1:3389–3402). Software for performing BLAST analyses is publicly available through the internet website of the National Center for Biotechnology information.

As used herein, "stringent hybridization conditions" or "stringency refers to conditions in a range from about 5° C. to about 20° C. or 25° C. below the melting temperature ($T_m$) of the target sequence and a probe with exact or nearly exact complementarity to the target. As used herein, the melting temperature is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL. 152: GUIDE TO MOLECULAR CLONING TECHNIQUES, San Diego; Academic Press, Inc. and Sambrook et al. (1989) MOLECULAR CLONING: A LABORATORY MANUAL, 2ND ED., VOLS. 1–3. Cold Spring Harbor Laboratory hereinafter. 'Sambrook'), both incorporated herein by reference). As indicated by standard references, a simple estimate of the $T_m$ value may be calculated by the equation: $T_m=8.15+0.41(\% G+C)$, when a nucleic acid is in aqueous solution at 1 M NaCl (see e.g., Anderson and Young, Quantitative Filter Hybridization in NUCLEIC ACID HYBRIDIZATION (1985)). Other references include more sophisticated computations which take structural as well as sequence characteristics into account for the calculation of $T_m$. The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, e.g., Sambrook, supra and Ausubel et al. supra. Typically, stringent hybridization conditions are salt concentrations less than about 1.0 M sodium ion, typically about 0.01 to 1.0 M sodium ion at pH 7.0 to 8.3, and temperatures at least about 30° C. for short probes (e.g., 10 to 50 nucleotides) and at least about 60° C. for long probes (e.g., greater than 50 nucleotides). As noted, stringent conditions may also be achieved with the addition of destabilizing agents such as formamide, in which case lower temperatures may be employed.

As used herein, the term "substantial identity," "substantial sequence identity," or "substantial similarity" in the context of nucleic acids, refers to a measure of sequence similarity between two polynucleotides. Substantial sequence identity can be determined by hybridization under stringent conditions, by direct comparison, or other means. For example, two polynucleotides can be identified as having substantial sequence identity if they are capable of specifically hybridizing to each other under stringent hybridization conditions. Other degrees of sequence identity (e.g., less than "substantial") can be characterized by hybridization under different conditions of stringency. Alternatively, substantial sequence identity can be described as a percentage identity between two nucleotide (or polypeptide) sequences. Two sequences are considered substantially identical when they are at least about 60% identical, preferably at least about 70% identical, or at least about 80% identical, or at least about 90% identical, or at least about 95% or 98% to 100% Identical. Percentage sequence (nucleotide or amino acid) identity is typically calculated by determining the optimal alignment between two sequences and comparing the two sequences. For example an exogenous transcript used for protein expression can be described as having a certain percentage of identity or similarity compared to a reference sequence (e.g., the corresponding endogenous sequence). Optimal alignment of sequences may be conducted using the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. U.S.A. 85: 2444, by computerized implementations of these algorithms (GAP, BESTFIT, FASTA, and TFASTA In the Wisconsin Genetics Software Package, Genetics Computer Group. 575 Science Dr., Madison, Wis.), or by inspection. The best alignment (i.e., resulting in the highest percentage of identity) generated by the various methods is selected. Typically these algorithms compare the two sequences over a "comparison window"(usually at least 18 nucleotides in length) to identify and compare local regions of sequence similarity, thus allowing for small additions or deletions (i.e., gaps). Additions and deletions are typically 20 percent or less of the length of the sequence relative to the reference sequence, which does not comprise additions or deletions. It is sometimes desirable to describe sequence identity between two sequences in reference to a particular length or region (e.g., two sequences may be described as having at least 95% identity over a length of at least 500 basepairs). Usually the length will be at least about 50, 100, 200, 300, 400 or 600 basepairs, amino acids, or other residues. The percentage of sequence identity is calculated by comparing two optimally aligned sequences over the region, of comparison, determining the number of positions at which the identical nucleic acid base (e.g., A, T. C, G, or U) occurs in both sequences to yield the number of matched positions, and determining the number (or percentage) of matched positions as compared to the total number of bases in the reference sequence or region of comparison.

When referring to an "activity" of an hTRT variant, a variant is considered to be active in an assay of it displays at least 40% of the activity characteristic of the hTRT polypeptide having the sequence set forth in FIG. 1 ("wild type"). A variant is considered to lack activity when it has less that 1% of the "wild type" activity. A variant with greater than 1% activity and less than 40% activity has intermediate activity."

As used herein, "conservative substitution," refers to substitution of amino acids with other amino acids having similar properties (e.g., acidic, basic, positively or negatively charged, polar or non-polar): The following six groups each contain amino acids that are conservative substitutions for one another: 1) alanine (A), serine (S), threonine (T); 2) aspartic acid (D), glutamic acid (E); 3) asparagine (N), glutamine (Q): 4) arginine (R), lysine (K); 5) isoleucine (1), leucine (L), methionine (M), valine (V); and 6) phenylalanine (F), tyrosine (Y), tryptophan (W) (see also, Creighton, 1984, PROTEINS, W.H. Freeman and Company).

All publications and patent documents cited in this application are incorporated by reference in their entirety and for all purposes to the same extent as if each individual publication or patent document were so individually denoted.

What is claimed is:

1. A polypeptide encoded by DNA that hybridizes to the sequence complementary to SEQ. ID NO:1 at 5° C. to 25° C. below $T_m$ in aqueous solution at 1 M NaCl,
wherein $T_m$ is the melting temperature of double-stranded DNA having the sequence of SEQ. ID NO:1 under the same reaction conditions;
wherein said polypeptide has one or more of the following deletions:
a) residues 560–565,
b) residues 930–934,
c) at least 10 consecutive amino acids from residues 326–415,
d) at least 10 consecutive amino acids from residues 637–660,
e) at least 10 consecutive amino acids from residues 748–766,
f) at least 10 consecutive amino acids from residues 1055–1071, or
g) at least 10 consecutive amino acids from residues 1084–1116 of SEQ. ID NO:2;
and wherein said polypeptide inhibits telomerase enzyme activity when introduced into a cell expressing human telomerase reverse transcriptase (hTRT) (SEQ. ID NO:2).

2. A polypeptide lacking telomerase enzyme activity, wherein said polypeptide comprises full-length hTRT (SEQ ID NO: 2), except for one or more deletions(s) selected from the group consisting of:
a) residues 560–565,
b) residues 930–934,
c) at least 10 consecutive amino acids between residues 323–450,
d) at least 10 consecutive amino acids between residues 637–660,
e) at least 10 consecutive amino acids between residues 748–766,
f) at least 10 consecutive amino acids between residues 1055–1071, or
g) at least 10 consecutive amino acids between residues 1084–1116.

3. A polypeptide lacking telomerase enzyme activity, wherein said polypeptide comprises full-length hTRT (SEQ. ID NO:2), except for one or more deletions(s) consisting essentially of residues 560–565, 930–934, 326–415, 637–660, 748–766, 1055–1071, or 1084–1116,
wherein said polypeptide lacks telomerase catalytic activity;
and wherein said polypeptide inhibits telomerase enzyme activity when introduced into a cell expressing hTRT.

4. A method of inhibiting telomerase catalytic activity, comprising introducing a polypeptide according to claim 1 into an environment containing telomerase reverse transcriptase.

5. A method of inhibiting telomerase catalytic activity in a cell, comprising expressing in the cell a nucleic acid encoding a polypeptide according to claim 1.

6. A method of inhibiting telomerase catalytic activity, comprising introducing a polypeptide according to claim 2 into an environment containing telomerase reverse transcriptase.

7. A method of inhibiting telomerase catalytic activity in a cell, comprising expressing in the cell a nucleic acid encoding a polypeptide according to claim 2.

8. A method of producing an inactive variant of telomerase reverse transcriptase in a cell, comprising transfecting the cell to express a polypeptide according to claim 2.

9. A method of inhibiting telomerase catalytic activity, comprising introducing a polypeptide according to claim 3 into an environment containing telomerase reverse transcriptase.

10. A method of inhibiting telomerase catalytic activity in a cell, comprising expressing in the cell a nucleic add encoding a polypeptide according to claim 3.

11. A method of producing an inactive variant of telomerase reverse transcriptase in a cell, comprising transfecting the cell to express a polypeptide according to claim 3.

* * * * *